United States Patent [19]
Lau et al.

[11] Patent Number: 6,071,932
[45] Date of Patent: Jun. 6, 2000

[54] CARBAZOLYPIPERINES AS GABA UPTAKE INHIBITORS

[75] Inventors: Jesper Lau, Farum; Jane Marie Lundbeck, Glostrup; Birgitte Soekilde, Vaerloese; Per Olaf Huusfeldt, Copenhagen, all of Denmark

[73] Assignee: British Technology Group Intercorporate Licensing Limited, London, United Kingdom

[21] Appl. No.: 08/945,045

[22] PCT Filed: May 1, 1996

[86] PCT No.: PCT/DK96/00199

§ 371 Date: Oct. 21, 1997

§ 102(e) Date: Oct. 21, 1997

[87] PCT Pub. No.: WO96/34863

PCT Pub. Date: Nov. 7, 1996

[30] Foreign Application Priority Data

May 5, 1995 [DK] Denmark ................................ 0521/95

[51] Int. Cl.[7] ........................ A61K 31/445; C07D 401/06
[52] U.S. Cl. ............................................ 514/323; 546/200
[58] Field of Search .............................. 514/323; 546/200

[56] References Cited

U.S. PATENT DOCUMENTS 4,539,407 9/1985 Stack et al. ................................ 546/87

5,834,482 11/1998 Lundbeck et al. ....................... 514/292

OTHER PUBLICATIONS

Hagen et al. "Synthesis of 6–substituted beta–carbolines that behave as . . . " CA 106:196295, 1987.

Primary Examiner—Ceila Chang
Attorney, Agent, or Firm—Nixon & Vanderhye

[57] ABSTRACT

A compound of formula (I).

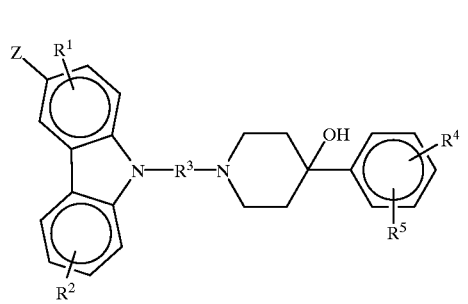

The present invention relates to thereutically active carbazole derivatives, a method of preparing the same and to pharmaceutical compositions comprising the compounds. The novel compounds are useful in treating a central nervous system ailment related to the inhibition of GABA uptake via the GAT-4 subtype carrier.

8 Claims, No Drawings

CARBAZOLYPIPERINES AS GABA UPTAKE INHIBITORS

This appication is a 371 of PCT/DK96/00199 filed May 1, 1996.

FIELD OF THE INVENTION

The present invention relates to novel substituted carbazole derivatives, to methods for their preparation, to pharmaceutical compositions containing them and to their use in the clinical treatment of abnormal functioning of the γ-aminobutyric acid neurotransmission system.

BACKGROUND OF THE INVENTION

γ-Aminobutyric acid (GABA) is the major inhibitory neurotransmitter in the central nervous system (CNS) (for review see Enna, 1983, Biochem. Pharmacol., 30, 907–15; Enna and Mohler, 1987, Raven Press, New York, 265–79; Lloyd and Morselli, 1987, Medical Biology, 65, (2–3), 159–65; Krogsgaard-Larsen, 1988, Medical Res. Reviews, 8, 1, 27–56; Schwartz, 1988, Biochem. Pharmacol. 27, 3369–76). GABA has been estimated to be present in 60–70% of all synapses within the CNS (Fahn, 1976, Raven Press, New York, 169–83). A reduction in GABA neurotransmission has been implicated in the etiology of a variety of neurological disorders including epilepsy Krogsgaard-Larsen et al., 1988, Medical Res. Reviews, 8, 1, 27–56; Löscher, 1985, Epilepsy and GABA Receptor Agonists: Basic and Therapeutic Research. L. E. R. S. Monograph. Vol. 3, G. Bartholoni, L. Bossi, K. G. Lloyd, P. L. Morselli (Eds.), Raven Press, New York, 109–18); Enna, 1981, Biochem. Pharmacol., 30, 907–14 and Neuropharmacology of Central Nervous System GABA and Behavioral Disorders, G. Palmer (Ed.). Academic Press, New York 1981, 507–25; Rebak et al., 1979, Science, 205, 211–13; Ross and Craig, 1981, J.Neurochem. 36, 1006).

The GABA uptake system has traditionally been classified as either neuronal or glial GABA uptake carriers, on the basis of pharmacological selectivity for specific GABA uptake inhibitors (for review see: Krogsgaard-Larsen, 1988, Medical Res. Reviews, 8, 1, 27–56; Schousboe et al., 1991, GABA Mechanisms in Epilepsy, G. Tunnicliff, B. U. Raess (Eds.) Wiley-Liss, New York, 165–87).

Several investigators (Gaustella et al., 1990, Science, 249, 1303–1306; Clark et al., 1992, Neuron 9, 337–348; Borden et al., 1992, J.Biol. Chem. 267, 21098–21104; Liu et al., 1993, J.Biol.Chem. 268, 2106–2112) have recently cloned, and sequenced, four subtypes of the rat and mouse GABA uptake carrier, whose pharmacology cannot be totally explained by the traditional neuronal and glial GABA uptake carriers. Gaustella et al., (1990, Science, 249, 1303–1306) and Nelson et al. (1990, FEBS Lett. 269, 181–184) reported on the cloning of GAT-1, which appears to be a neuronal GABA uptake carrier due to its high sensitivity to nipecotic acid (Gaustella et al., 1990, Science, 249, 1303–1306), and lipophilic nipecotic acid based compounds and distribution within the central nervous system (CNS) (Radian et al., 1990, J.Neurosci. 10, 1319–1330; Mabjeesh et al., 1992, J.Biol.Chem. 267, 2563–68). GAT-1 is not present outside the CNS (Nelson et al., 1990, FEBS Lett. 269, 181–184; Liu et al., 1992, FEBS. Lett. 305, 110–114). GAT-2 was initially cloned by Lopez-Corruera (1992, J.Biol.Chem. 267, 17491–17493) and is present in the CNS, kidney and liver, and has a pharmacology resembling the glial GABA uptake carrier characterized in primary cell culture. GAT-3 which was initially cloned by Liu et al., (1993, J.Biol.Chem. 267, 2106–2112), appears to be under developmental control, as GAT-3 mRNA is highly expressed in neonatal brain, but weakly expressed in adult brain. GAT-3 is also present in kidney and liver. GAT-4 (Liu et al., 1993, J.Biol.Chem. 268, 2106–2112; also termed GAT-B by Clark et al., (1992, Neuron 9, 337–348) and GAT-3 by Borden et al., (1992, J.Biol.Chem. 267, 21098–21104)), cDNA hybridized only in the CNS, and the mRNA for GAT-4 is highly enriched in the brain stem, but not present in the cerebellum or cerebral cortex. While GAT-4 has been shown to transport β-alanine, it appears to have neuronal localization (Clarke et al., 1992, Neuron 9, 337–348).

The distribution of GAT-1, closely resembles the previously reported distribution of $^3$H-Tiagabine receptor autoradiography (Suzdak et al., 1994, Brain Research, 647(2), 231–41), as would be expected due to the high affinity of lipophilic nipecotic acid based GABA uptake inhibitors for the GAT-1 transporter (Clarke et al., 1992, Neuron 9, 337–348). While in situ hybridization has revealed the presence of GAT-4 mRNA in the CNS, there has been no direct demonstration of a discretely localized neuronal GABA uptake carrier, which is not sensitive to lipophilic nipecotic acid based GABA uptake inhibitors.

The inhibition of GABA uptake results in enhanced availability of this inhibitory neurotransmitter in the synaptic cleft and thus to increased GABA'ergic activity. Increased GABA'ergic activity can be useful in the treatment, for example of anxiety, pain and epilepsy, as well as muscular and movement disorders (see, for example, P. Krogsgaard-Larsen et al., Progress in Medicinal Chemistry, 1985, 22, 68–112).

A well-known and potent inhibitor of GABA uptake from the synaptic cleft into presynaptic nerve terminals and glial cells is, for example, 3-piperidinecarboxylic acid (nipecotic acid). However, being a relatively polar compound and therefore unable to cross the blood-brain barrier, 3-piperidinecarboxylic acid itself has found no practical utility as a drug.

In U.S. Pat. No. 4,383,999 and U.S. Pat. No. 4,514,414 and in EP 236342 as well as in EP 231996 some derivatives of N-(4,4-disubstituted-3-butenyl)azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. Further, in WO 9107389 and WO 9220658, N-substituted azacyclic carboxylic acids are claimed as inhibitors of GABA uptake. EP 221572 claims that 1-aryloxyalkylpyridine-3-carboxylic acids are inhibitors of GABA uptake.

According to Yunger, L. M. et al., J.Pharm.Exp.Ther. 1984, 228, 109, N-(4,4-diphenyl-3-buten-1-yl)nipecotic acid (designated SK&F 89976A), N-(4,4-diphenyl-3-buten-1-yl)guvacine (designated SK&F 100330A), N-(4,4-diphenyl-3-buten-1-yl)-homo-β-proline (designated SK&F 100561) and N-(4-phenyl-4-(2-thienyl)-3-buten-1-yl) nipecotic acid (designated SK&F 100604J) are orally active inhibitors of GABA uptake. These data are summarized in Krogsgaard-Larsen, P. et al., Epilepsy Res. 1987, 1, 77–93.

The above cited references all disclose compounds inhibiting the uptake of GABA via the GAT-1 subtype carrier.

U.S. Pat. No. 4,539,407 discloses β-carboline-3-carboxylate ester derivatives having anticonvulsant activity.

The present invention is directed to identifying novel compounds with affinity for the neuronal subtype of the GABA uptake carrier whose pharmacology resembles that of GAT-4.

DESCRIPTION OF THE INVENTION

The present invention relates to novel substituted carbazole derivatives of formula I

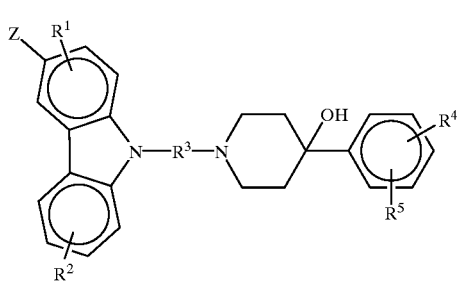

wherein
- $R^1$ and $R^2$ independently are hydrogen, halogen, hydroxy, nitro, $-(CH_2)_n-(C=O)-(CH_2)_mCH_3$, $-NR^9R^{10}$, $-SONR^{11}R^{12}$, $-COOR^{13}$, $-CONR^{14}R^{15}$, $C_{1-6}$-alkyl, $C_{1-6}$-alkoxy, trifluoromethyl or trifluoromethoxy wherein $R^9$, $R^{10}$, $R^{11}$, $R^{12}$, $R^{13}$, $R^{14}$ and $R^{15}$ independently are hydrogen, $C_{1-6}$-alkyl, $C_{2-6}$-alkenyl or $C_{2-6}$-alkynyl, and wherein n and m independently are 0, 1, 2, 3 or 4; and
- $R^3$ is $C_{1-5}$-alkylene optionally substituted with one or two $C_{1-6}$-alkyl; and
- $R^4$ is hydrogen or $C_{1-6}$-alkyl; and
- $R^5$ and $R^6$ independently are hydrogen, halogen, hydroxy, nitro, $-NR^{16}R^{17}$, $-COOR^{18}$, $C_{1-6}$-alkyl, $C_{1-6}$-alkoxy, trifluoromethyl or trifluoromethoxy wherein $R^{16}$, $R^{17}$ and $R^{18}$ independently are hydrogen, $C_{1-6}$-alkyl, $C_{2-6}$-alkenyl or $C_{2-6}$-alkynyl; and
- Z is $-(CH_2)_p-(C=O)-(CH_2)_qCH_3$, $-COOR^{19}$,

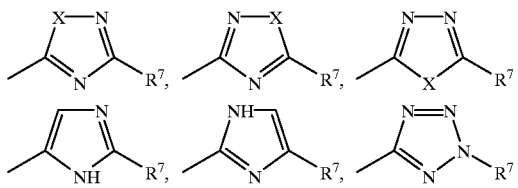

wherein p and q independently are 0, 1, 2, 3 or 4; and
- $R^{19}$ is hydrogen, $C_{1-6}$-alkyl, $C_{2-6}$-alkenyl or $C_{2-6}$-alkynyl; and
- X is $-NH-$, oxygen or sulphur; and
- $R^7$ is hydrogen, $C_{1-6}$-alkyl, $C_{2-6}$-alkenyl, $C_{2-6}$-alkynyl, phenyl, $C_{3-7}$-cycloalkyl, $-OR^8$ or $-SR^8$ wherein $R^8$ is hydrogen or $C_{1-6}$-alkyl; or a pharmaceutically acceptable salt thereof.

The compounds of formula I may exist as geometric and optical isomers and all isomers and mixtures thereof are included herein. Isomers may be separated by means of standard methods such as chromatographic techniques or fractional crystallization of suitable salts.

The compounds according to the invention may optionally exist as pharmaceutically acceptable acid addition salts.

Examples of such salts include inorganic and organic acid addition salts such as hydrochloride, hydrobromide, sulphate, phosphate, acetate, phthalate, fumarate, maleate, citrate, lactate, tartrate, oxalate, or similar pharmaceutically acceptable inorganic or organic acid addition salts, and include the pharmaceutically acceptable salts listed in Journal of Pharmaceutical Science, 66, 2 (1977) which are hereby incorporated by reference.

Alkyl, alkenyl and alkynyl are intended to mean straight or branched alkyl, alkenyl or alkynyl chains.

The compounds of formula I have a greater lipophilicity—and thus a greater availability to the brain—as well as a far higher affinity to the GABA uptake sites than the parent compounds without the carbazole moiety.

It has been demonstrated that the novel compounds of formula I which selectively inhibit the uptake of GABA, via the GAT-4 subtype carrier, from the synaptic cleft possess useful pharmacological properties in the central nervous system, in that they cause a selective enhancement of GABA'ergic activity. Compounds of formula I may be used to treat for example, pain, anxiety, extrapyrimidinal dyskinesia, epilepsy and certain muscular and movement disorders. They are also useful as sedatives, hypnotics and antidepressants.

The invention also relates to a method of preparing the above mentioned compounds of formula I. These methods comprise:

Method A:

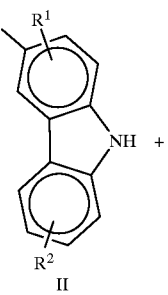

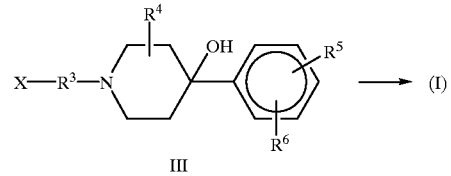

A compound of formula II wherein $R^1$, $R^2$ and Z are as defined above, may be reacted with an azaheterocyclic compound of formula III wherein $R^3$, $R^4$, $R^5$ and $R^6$ are as defined above and X is a suitable leaving group such as halogen, p-toluene sulphonate or mesylate. This alkylation reaction may be carried out in a suitable solvent such as acetone, dibutylether, 2-butanone, tetrahydrofuran, methylisobutylketone, methylisopropylketone, toluene, benzene or DMF in the presence of a base e.g. potassium carbonate, sodium hydride or potassium tert.-butoxide at a temperature up to reflux for the solvent used for e.g. 1 to 200 h.

Method B:

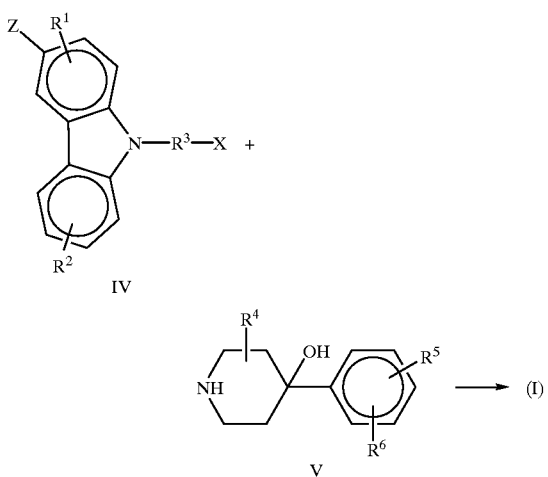

A compound of formula IV wherein $R^1$, $R^2$, $R^3$, Z and X are as defined above may be reacted with an azaheterocyclic compound of formula V wherein $R^4$, $R^5$ and $R^6$ are as defined above. This alkylation may be carried out in a suitable solvent as defined above in the presence of a base as defined above and a catalyst e.g. an alkali metal iodide at a temperature up to reflux for the solvent used for e.g. 1 to 200 h.

Method C:

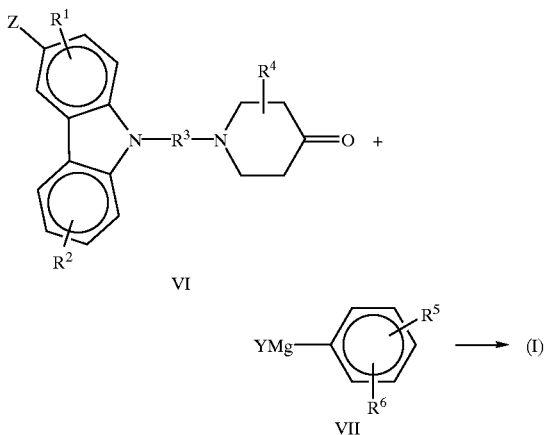

An azaheterocyclic ketone of formula VI wherein $R^1$, $R^2$, $R^3$, $R^4$ and Z are as defined above may be reacted with a Grignard reagent of formula VII wherein $R^5$ and $R^6$ are as defined above and Y is chloro, bromo or iodo. This reaction may be carried out in a suitable solvent such as diethylether, THF, toluene or benzene at a suitable temperature up to reflux temperature for the solvent used for e.g. 1 to 5 h.

Pharmacological Methods $^3$H-GABA uptake was measured by a modification of the method of Fjalland et al., (1978). A crude membrane preparation was prepared from selected brain areas by homogenization in 20 ml of ice-cold 0.32 M sucrose with a hand driven teflon/glass Potter-Elvehjem homogenizer. The homogenate was centrifuged at 4° C. for 10 min. at 1.000×g, and the pellet was discarded. The supernatant was recentrifuged at 4° C. for 20 min. at 20.000×g. The pellet was then homogenized in 50 volumes 0.32 M sucrose. To 300 µl uptake-buffer (200 nM NaCl, 15.3 mM KCl, 6.67 mM $MgSO_4$, 3.83 mM $CaCl_2$, 16.67 mM glucose, 66.67 mM Tris, pH 7.5 at 30° C.) was added 1-(2-(((diphenylmethylene)amino)oxy)ethyl)-1,2,5,6-tetrahydro-3-pyridinecarboxylic acid (NNC 05–0711) (1 mM final concentration), 100 µl test substance and 50 µl tissue suspension. The samples were mixed and incubated at 30° C. for 8 min. Then $^3$H-GABA (0.9 nM final concentration) and unlabelled GABA (25 nM final concentration) was added, and the incubation was continued for an additional 8 min. The reaction was terminated by rapid filtration through Whatman GF/F glass fiber filters under vacuum. The filters were then washed twice in 10 ml of ice-cold isotonic saline, and the tritium trapped on the filters was quantified by conventional scintillation spectroscopy. Non-GABA uptake carrier mediated uptake of $^3$H-GABA was determined in the presence of 500 µl nipecotic acid.

Values for non-GABA uptake carrier mediated uptake of $^3$H-GABA for some representative compounds are recorded in Table I.

TABLE 1

| Non-GABA uptake carrier mediated uptake of $^3$H-GABA. | |
| --- | --- |
| Compound No. | $IC_{50}$ (nM) in vitro |
| 2 | 473 |
| 4 | 1128 |
| 5 | 1615 |
| 6 | 1632 |
| 7 | 592 |
| 11 | 1478 |
| 13 | 7858 |
| 14 | 3159 |
| 16 | 1703 |
| 18 | 2882 |
| 20 | 3857 |
| 23 | 3095 |
| 27 | 1729 |
| 28 | 3405 |
| 29 | 3910 |

For the above indications the dosage will vary depending on the compound of formula I employed, on the mode of administration and on the therapy desired. However, in general, satisfactory results are obtained with a dosage of from about 0.5 mg to about 1000 mg, preferably from about 1 mg to about 500 mg of compounds of formula I, conveniently given from 1 to 5 times daily, optionally in sustained release form. Usually, dosage forms suitable for oral administration comprise from about 0.5 mg to about 1000 mg, preferably from about 1 mg to about 500 mg of the compounds of formula I admixed with a pharmaceutical carrier or diluent. with a pharmaceutical carrier or diluent.

The compounds of formula I may be administered in pharmaceutically acceptable acid addition salt form or where possible as a metal or a lower alkylammonium salt.

This invention also relates to pharmaceutical compositions comprising a compound of formula I or a pharmaceutically acceptable salt thereof and, usually, such compositions also contains a pharmaceutical carrier or diluent. The compositions containing the compounds of this invention may be prepared by conventional techniques and appear in conventional forms, for example capsules, tablets, solutions or suspensions.

The pharmaceutical carrier employed may be a conventional solid or liquid carrier. Examples of solid carriers are lactose, terra alba, sucrose, talc, gelatin, agar, pectin, acacia, magnesium stearate and stearic acid. Examples of liquid carriers are syrup, peanut oil, olive oil and water.

Similarly, the carrier or diluent may include any time delay material known to the art, such as glyceryl monostearate or glyceryl distearate, alone or mixed with a wax.

If a solid carrier for oral administration is used, the preparation can be tabletted, placed in a hard gelatin capsule in powder or pellet form or it can be in the form of a troche or lozenge. The amount of solid carrier will vary widely, but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

Generally, the compounds of this invention are dispended in unit dosage form comprising 50–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet, which may be prepared by conventional tabletting techniques contains:

| Core: | | |
|---|---|---|
| Active compound (as free compound or salt thereof) | | 100 mg |
| Colloidal silicon dioxide (Aerosil,TM) | | 1.5 mg |
| Cellulose, microcryst. (Avicel,TM) | | 70 mg |
| Modified cellulose gum (Ac-Di-Sol,TM) | | 7.5 mg |
| Magnesium stearate | | |
| Coating: | | |
| HPMC | approx. | 9 mg |
| *Mywacett,TM 9-40 T | approx. | 0.9 mg |

*Acylated monoglyceride used as plasticizer for film coating.

The route of administration may be any route, which effectively transports the active compound to the appropriate or desired site of action, such as oral or parenteral e.g. rectal, transdermal, subcutaneous, intravenous, intraurethral, intramuscular, topical, intranasal, ophthalmic solution or an ointment, the oral route being preferred.

EXAMPLES

The process for preparing compounds of formula I is further illustrated in the following examples which however are not to be construed as limiting.

Hereinafter, DMF is N,N-dimethylformamide, TEA is triethylamine, MIBK is methyl isobutylketone, TLC is thin layer chromatography and THF is tetrahydrofuran, $CDCl_3$ is deuterio chloroform and DMSO-$d_6$ is hexadeuterio dimethylsulfoxide. The structures of the compounds are confirmed by either elemental analysis or NMR, where peaks assigned to characteristic protons in the title compounds are presented where appropriate. NMR shifts ($\delta$) are given in parts per million (ppm). M.p. is melting point and is given in ° C. Column chromatography was carried out using the technique described by W. C. Still et al, J. Org. Chem. 1978, 43, 29232925 on Merck silica gel 60 (Art. 9385). Compounds used as starting materials are either known compounds or compounds which can readily be prepared by methods known per se.

Example 1

3-Chloro-1-(9H-carbazol-9-yl)propane/3-Bromo-1-(9H-carbazol-9-yl)propane (Compound 1)

Carbazole (50.0 g, 0.3 mol) was dissolved in dry DMF (1.5 L). NaH (60% in oil, 18.8 g, 0.45 mol) was added under a nitrogen atmosphere. The reaction mixture was stirred at ambient temperature for 3 h. To the resulting sodium salt was carefully added under vigorous stirring a solution of 1-bromo-3-chloropropane in dry DMF (0.5 L). The mixture was stirred at room temperature for 10 h. The solvent was removed in vacuo. The residual oil was dissolved in $CH_2Cl_2$ (350 mL), washed with water (3×100 ml), dried ($MgSO_4$), filtered and the solvent removed in vacuo to give a yellow oil. The oil was triturated with cold n-heptane (3×50 mL), and the precipitate collected. This afforded the title compound (48.3 g, 66%) as a yellow solid. M.p. 39–40° C. $^1$H-NMR ($\delta$ $CDCl_3$): 2.3–2.5 (m, 2H); 3.4 (t, 1H); 3.55 (t, 1H); 4.55 (d, t, 2H); 7.35 (m, 2H); 7.5 (d, 2H); 8.1 (d, 2H). The product was isolated as an 1:1 mixture of the 3-bromo- and 3-chloro-derivatives.

Example 2

1-(3-(9H-Carbazol-9-yl)-1-propyl)-4-(4-methoxyphenyl)piperidin-4-ol hydrochloride (Compound 2)

4-(4-Methoxyphenyl)piperidin-4-ol (1.0 g, 0.004 mol) was dissolved in dry DMF (30 mL). $K_2CO_3$ (2.8 g, 0.021 mol), Kl (0.7 g, 0.004 mol) and compound 1 (1.0 g, 0.004 mol) were added, and the resulting mixture was stirred at 90° C. for 96 h. The reaction mixture was filtered and the solvent was removed in vacuo. The residual oil was dissolved in ethyl acetate (200 mL), washed twice with water (75 mL), dried ($MgSO_4$), filtered and concentrated to dryness in vacuo. The crude product was purified on a silica gel column (Eluent: $CH_2Cl_2$/ethanol/25% $NH_4OH$ (aq) (92.75:7:0.25)). The isolated product was acidified with 2M HCl (g) in diethylether. The resulting solid was crystallized from ethanol to give the title compound 0.7 g (39%). M.p. 159–162° C.

Example 3

3-Iodo-1-(9H-carbazol-9-yl)propane (Compound 3)

Compound 1 17.5 g, 0.072 mol) was dissolved in acetone (800 mL) and NaI (51.25 g, 0.342 mol) was added. The resulting mixture was refluxed for 8 hours and left at room temperature overnight. The reaction mixture was filtered and the solvent removed in vacuo. The residual oil was dissolved in $CH_2Cl_2$ (500 mL) and washed with 5% $Na_2S_2O_3$ (aq) (150 mL), water (200 mL), brine (150 mL), dried ($MgSO_4$), filtered and concentrated to dryness in vacuo, giving 17 g of a solid. Crystallization from ethyl acetate/n-heptane (25:100) gave the title compound 7.55 g (31%). M.p. 152–156° C.

Example 4

1-(3-(9H-Carbazol-9-yl)-1-propyl)-4-phenylpiperidin-4-ol hydrochloride (Compound 4)

Compound 3 (2.5 g, 0.0054 mol ) was dissolved in dry DMF (80 mL), 4-phenylpiperidin-4-ol (0.82 g, 0.0046 mol) and TEA (0.55 g, 0.0054 mol) were added. The resulting mixture was stirred at 50–60° C. for 12 h. The reaction mixture was evaporated in vacuo, and the residual oil purified on a silica gel column (Eluent: 1) $CH_2Cl_2$ 2) $CH_2Cl_2$/methanol (95:5)). The product was acidified with 2M HCl(g) in diethylether to give the title compound 1.94 g (72%) as a solid. M.p. 145–150° C.

Example 5

1-(3-(9H-Carbazol-9-yl)-1-propyl)-4-(2-methoxyphenyl)piperidin-4-ol hydrochloride (Compound 5)

Compound 1 (0.879 g, 0.0036 mol ) was dissolved in methylisobutylketone (MIBK) (80 mL). 4-(2-

Methoxyphenyl)piperidin-4-ol (1.123 g, 0.0054 mol) and $K_2CO_3$ (1.99 g, 0.0145 mol) were added. The resulting mixture was stirred at reflux temperature for 12 h. The reaction mixture was filtered and the solvent evaporated in vacuo. The residual oil was purified on a silica gel column (Eluent: $CH_2Cl_2$/ethanol/25% $NH_4OH$ (aq) (92.75:7:0.25)). The product was acidified with 2M HCl(g) in diethylether, to give the title compound 1.1 g (68%). M.p. decomposes at 228° C.

Example 6

1-(3-(9H-Carbazol-9-yl)-1-propyl)-3-methyl-4-(4-methoxyphenyl)piperidin-4-ol hydrochloride (Compound 6)

Compound 1 (3.08 g, 0.0126 mol) was dissolved in MIBK (60 mL) 4-(4-methoxyphenyl)-3-methylpiperidin-4-ol (4.0 g, 0.0189 mol) and $K_2CO_3$ (6.97 g, 0.0505 mol) were added. The resulting mixture was stirred at reflux temperature for 12 h. The reaction mixture was filtered and the solvent evaporated in vacuo. The residual oil was purified on a silica gel column (Eluent: $CH_2Cl_2$/ethanol/25% $NH_4OH$ (aq) (92.5:7:0,5)) to give 3.69 g (69%) of a white solid. A 1.5 g sample was acidified with 2M HCl(g) in diethylether, giving the title compound 1.42 g. M.p. decomposes at 230.5–231.5° C.

Example 7

1-(3-(9H-Carbazol-9-yl)-1-propyl)-4-(4-chlorophenyl)piperidin-4-ol hydrochloride (Compound 7)

Compound 3 (2.58 g, 0.0056 mol) was dissolved in dry DMF (80 mL), 4-(4-chlorophenyl)piperidin-4-ol (1.0 g, 0.0047 mol) and $K_2CO_3$ (0.57 g, 0.0056 mol) were added. The resulting mixture was stirred at 50–60° C for 12 h and at room temperature for 48 h. The reaction mixture was concentrated to dryness in vacuo and $CH_2Cl_2$ (100 mL) was added. The organic phase was washed with 5% $NaHCO_3$ (aq) (100 mL), brine (50 mL), dried ($MgSO_4$), filtered and the solvent evaporated in vacuo, to give 4.8 g of an oil. The residual oil was purified on a silica gel column (Eluent: ethyl acetate/n-heptane (1:1)). The product was acidified with 2M HCl(g) in diethylether, giving the title compound 1.6 g (75%). M.p. 194.5–195.5° C.

Example 8

(2S)-3-Bromo-2-methyl-1-((tetrahydropyran-2-yl)oxy)propane (Compound 8)

Pyridinium-4-toluenesulfonate (PPTs) (0.18g, 0.072 mmol) was dissolved in dry $CH_2Cl_2$(30 mL), (S)-(+)-3-bromo-2-methyl-1-propanol (1.1 g, 7.2 mmol) and 2,3-dihydro-4H-pyran (DHP) (0.60 g, 7.2 mmol) were added. The mixture was stirred under a $N_2$ atmosphere at room temperature for 5 h. Diethylether (20 mL) was added and the resulting mixture was washed with brine (820 mL), dried ($MgSO_4$) and the solvents were removed In vacuo. This afforded a crude product which on ball-tube-distillation (90° C./0.1 mmHg) gave the title compound 1.07 g (63%).

Example 9

(2S)-3-(9H-Carbazol-9-yl)-2-methyl-1-((tetrahydropyran-2-yl)oxy)propane (Compound 9)

Carbazole (1.42 g, 0.0085 mol) was dissolved in dry DMF (40 mL) and NaH (60% dispersion in oil) (0.443 g, 0.0111 mol) was added. After stirring at ambient temperature for 45 min compound 8 (2.02 g, 0.0085 mol) was added and stirring continued at room temperature for 18 h. Water (20 mL) was added. Extraction with $CH_2Cl_2$ (3×20 ml), drying of the organic phases ($MgSO_4$) and evaporation of the solvents in vacuo afforded an oil. Purification of the crude product twice on a silica gel column (1: Eluent: ethyl acetate/n-heptane(1:8), and 2: Eluent: ethyl acetate/toluene (1:9)) gave the title compound 0.59 g (21%) as an oil.

Example 10

(S)-3-(9H-Carbazol-9-yl)-2-methyl-1-propanol (Compound 10)

Compound 9 (0.47 g, 0.0145 mol) was mixed with pyridinium-4-toluene-sulfonate (PPTs) (0.037 g, 0.15 mmol) in ethanol (20 mL). The resulting mixture was stirred at 50° C. for 24 h. The solvent was evaporated in vacuo. Purification of the crude product on a silica gel column (Eluent: ethyl acetate/n-heptane (1:1)) gave the title compound 0.226 g (65%) as a solid. M.p. 80–81° C.

Example 11

(S)-1-((3-(9H-Carbazol-9-yl)-2-methyl)-1-propyl)-4-ph-enylpiperidin-4-ol hydrochloride (Compound 11)

Compound 10 (0.22 g, 0.0009 mol) was dissolved in dry diethylether (30 mL), TEA (0.23 g, 0.0023 mol) and a solution of methanesulfonylchloride (0.158 g, 0.0014 mol) in dry diethylether (5 mL) were added. The resulting mixture was stirred under a $N_2$ atmosphere at ambient temperaure for 5 h. After addition of water (10 mL) the reaction mixture was stirred vigorously for 10 min, separation of the phases, drying of the organic phase ($MgSO_4$) and evaporation of the solvent in vacuo afforded the mesylate (0.290 g, 99%). The mesylate was dissolved in MIBK (25 mL). $K_2CO_3$ (0.380 g, 0.0028 mol) and 4-phenylpiperidin-4-ol (0.196 g, 0.0011 mol) were added. The resulting mixture was stirred under a $N_2$ atmosphere at 70° C. for 72 h. The solvent was evaporated in vacuo. Addition of water (15 mL), extraction with $CH_2Cl_2$ (3×20 ml), drying of the organic phases ($MgSO_4$) and evaporation of the solvent in vacuo gave an oil. The residual oil was purified on a silica gel column (Eluent: $CH_2Cl_2$/MeOH (9:1)), and acidified with 2M HCl(g) in diethylether. This afforded the title compound 0.155 g (39%). M.p. 239° C.

Example 12

(R)-3-(9H-Carbazol-9-yl)-2-methyl-1-propanol (Compound 12)

Carbazole (0.50 g, 3.0 mmol) was dissolved in dry DMF (20 mL) and NaH (60% dispersion in oil) (0.36 g, 9.0 mmol) was added. The resulting mixture was stirred under a $N_2$ atmosphere at 25° C. for 30 min. (R)-(−)-3-Bromo-2-methyl-1-propanol (1.14 g, 7.5 mmol) was added in 4 portions over a period of 10 min, and the mixture stirred at 45° C. for 48 h. The solvent was removed in vacuo. Addition of water (20 mL), extraction with $CH_2Cl_2$ (3×20 ml), drying of the organic phases ($MgSO_4$) and evaporation of the solvent in vacuo gave an oil that was purified on a silica gel column (Eluent: ethyl acetate/n-heptane (1:1)). This afforded the title compound 0.16 g (23%) as a white solid. M.p. 80–81° C.

Example 13

(R)-1-((3-(9H-Carbazol-9-yl)-2-methyl)-1-propyl)-4-phenylpiperidin-4-ol hydrochloride (Compound 13)

The compound was synthesized in the same manner as compound 11, by using compound 12 (0.16 g, 0.7 mmol) as starting material. The mesylate was prepared by reaction with methanesulfonylchloride (0.115 g, 1.0 mmol) and TEA. (0.169 g, 1.7 mmol) in dry diethylether (20 mL). The mesylate was converted into the title compound after reaction with 4-phenylpiperidin-ol (0.142 g, 2.0 mmol) and $K_2CO_3$ (0.277 g, 2.0 mmol) in MIBK (20 mL), as described for compound 11. Purification on a silica gel column and precipitation of the compound as the hydrochloride salt afforded the title compound 0.080 g (20%). M.p. 239° C.

Example 14

1-(3-(9H-Carbazol-9-yl)-1-propyl)-4-(2-tolyl) piperidin-4-ol hydrochloride (Compound 14)

4-(2-Tolyl)piperidin-4-ol (0.71 g, 3.7 mmol), compound 1 (1.81 g, 7.4 mmol), $K_2CO_3$ (2.57 g, 18.6 mmol) and KI (0.31 g, 1.9 mmol) in dry DMF (40 mL), were stirred for 7d at 90–100° C. After evaporation of the solvent in vacuo, water (20 mL) was added. The resulting mixture was extracted with $CH_2Cl_2$ (3×30 ml), and the combined organic phases were dried ($MgSO_4$). The solvent was evaporated in vacuo and the residue purified on a silica gel column (Eluent: $CH_2Cl_2$/methanol (95:5)). This afforded the free base (0.288 g, 20%) as a solid. Conversion of a 100 mg sample into the hydrochloride salt with 2M HCl(g) in diethylether gave the title compound 0.035 g (6%). M.p. 183–185° C.

Example 15

3-Chloro-1-(3-ethyl-9H-carbazol-9-yl)propane/3-Bromo-1-(3-ethyl-9H-carbazol-9-yl)propane (Compound 15)

The compound was synthesized in the same manner as in example 1. Treatment of 3-ethylcarbazole (2.0 g, 0.0102 mol) with NaH (0.27 g, 0.0112 mol) succeeded by the addition of 1-bromo-3-chloropropane (1.77 g, 0.0112 mol) in DMF gave the title compound 2.3 g (82%) as a yellow oil. $^1$H-NMR (δ, $CDCl_3$): 1.35 (t, 3H); 2.4 (m, 2H); 2.8 (q, 2H); 3.35 (t, 1H); 3.45 (t, 1H); 4.35 (t, 2H); 7–7.4 (m, 4H); 7.9 (s, 2H); 8.1 (d, 2H). The product was isolated as an 1:1 mixture of the 3-bromo- and 3-chloro derivatives.

Example 16

1-(3-(3-Ethyl-9H-carbazol-9-yl)-1-propyl)-4-phenylpiperidin-4-ol (Compound 16)

The compound was synthesized by mixing compound 15 (2.17 g, 0.0080 mol), 4-phenylpiperidin-4-ol (1.21 g, 0.0069 mol) and TEA (2.44 g, 0.0240 mol) in DMF, in the same manner as illustrated in example 2, to give the title compound 0.22 g (6%). M.p. 215.5–216° C.

Example 17

3-Chloro-1-(3-nitro-9H-carbazol-9-yl)propane (Compound 17)

The compound was synthesized by mixing 3-nitrocarbazole (0.5 g, 0.0024 mol), NaH (0.06 g, 0.0026 mol) and 1-bromo-3-chloropropane (0.41 g,

Example 18

1-(3-(3-Nitro-9H-carbazol-9-yl)-1-propyl)-4-phenylpiperidin-4-ol hydrochloride (Compound 18)

The compound was synthesized by mixing compound 17 (0.47 g, 0.0016 mol), 4-phenylpiperidin-4-ol (0.29 g, 0.0016 mol) and TEA (0.66 g, 0.0065 mol) in DMF, in the same manner as illustrated in example 2, to give the title compound 0.29 g (39%). M.p. decomposes at 233–234° C.

Example 19

3-Chloro-1-(3-acetyl-9H-carbazol-9-yl)propane (Compound 19)

3-Acetylcarbazole (1.0 g, 0.0048 mol) was dissolved in dry DMF (20 mL) and NaH (50% in oil) (0.13 g, 0.0053 mol) was added. The resulting mixture was stirred at room temperature for 1 h. The reaction mixture was added dropwise to a solution of 1-bromo-3-chloropropane (0.83 g, 0.0053 mol) in DMF (20 mL). The resulting mixture was stirred under a $N_2$ atmosphere for 60 h. The solvent was removed in vacuo, and the residue was purified on a silica gel column (Eluent: $CH_2Cl_2$). This afforded the title comoound 0.70 g (51%) as a solid. M.p. 109–111° C.

Example 20

1-(3-(3-Acetyl-9H-carbazol-9-yl)-1-propyl)-4-phenylpiperidin-4-ol hydrochloride (Compound 20)

To a solution of compound 19 (0.70 g, 0.0025 mol) in DMF (40 mL), 4-phenylpiperidin-4-ol (0.43 g, 0.0025 mol) and TEA (1.01 g, 0.010 mol) were added. The reaction mixture was heated at 80° C. under a $N_2$ atmosphere for 72 h. The solvent was evaporated in vacuo gave, and the residue purified on a phenylpiperidin-4-ol (0.43 g, 0.0025 mol) and TEA (1.01 g, 0.010 mol) were added. The reaction mixture was heated at 80° C. under a $N_2$ atmosphere for 72 h. The solvent was evaporated in vacuo gave, and the residue purified on a silica gel column (Eluent: $CH_2Cl_2$/methanol (19:1)). Acidification with 1.22 M HCl in diethylether afforded the title compound (0.50 g, 43%) as a solid. M.p. decomposes at 225–226° C.

Example 21

General Procedure for the Synthesis of Piperidin-4-ols:

1-Acetyl-4-(2-tolyl)piperid in-4-ol

To magnesium turnings (1.82 g, 0.075 mol), covered by dry diethylether (100 mL) under a $N_2$ atmosphere was dropwise added 2-bromotoluene (14.22 g, 0.083 mol). After addition of approximately ⅓ of the bromide the reaction was initiated by gently heating the mixture. The remaining 2-bromotoluene was added over a period of 5 min. When addition was completed the resulting mixture was refluxed for 1.5 h. 1-Acetyl-4-piperidone (9.53 g, 0.068 mol) was added dropwise at ambient temperature and diethylether (100 mL) was added. The reaction mixture was stirred at reflux temperature for 30 min and 1 h at room temperature. 4M $NH_4Cl$ (aq) (100 mL) was added and the phases were separated. The organic phase was washed with brine (10 mL), dried ($MgSO_4$) and the solvent evaporated in vacuo. The residual oil was purified on a silica gel column (Eluent: $CH_2Cl_2$/methanol (19:1)) to give the title compound 1.31 g (8%). M.p. 145–146° C.

4-(2-Tolyl)piperidin-4-ol hydrochloride

A mixture of 1-acetyl-4-(2-tolyl)piperidin-4-ol (1.25 g, 0.0054 mol), ethanol (30 mL) and 1M NaOH (aq) (25 mL) was refluxed for 18 h. The solvents were evaporated in vacuo and water (30 mL) was added. Extraction with $CH_2Cl_2$ (3×30 ml), drying of the organic phases ($MgSO_4$) and evaporation of the solvent in vacuo gave the free base of the product (0.800 g, 78%) as a solid. An analytical sample (90 mg) was converted to the hydrochloride salt with 2M HCl(g) in diethylether and recrystallized from ethanol/diethylether. This afforded the title compound 0.034 g (32%). M.p. 250–251° C.

Example 22

1-(3-(9H-Carbazol-9-yl)-2-hydroxy-1-propyl)-4-(4-methoxyphenyl)piperidin-4-ol hydrochloride (Compound 21)

4-(4-Methoxyphenyl)piperidin-4-ol (0.50 g, 0.0024 mol) was dissolved in 4-methyl-pentan-2-one (35 mL), $K_2CO_3$ (1.33 g, 0.0096 mol) and 9-(3-chloro-2-hydroxy-1-propyl)carbazole (0.42 g, 0.0016 mol) were added, and the resulting mixture was stirred at reflux temperature overnight. The reaction mixture was filtered and the solvent was removed in vacuo. The residual oil was purified on a silica gel column (Eluent: $CH_2Cl_2$/ethanol/25% $NH_4OH$ (aq) (92.75:7:0.25)). The product was acidified with 2M HCl(g) in diethyl ether, to give the title compound 0.39 g (51%). M.p. decomposes at 125° C.

Example 23

3-Chlorobutanoylchloride (Compound 22)

3-Chlorobutanoic acid (2.38 g, 0.019 mol) was carefully added to thionyl-chloride (2.77 g, 0.023 mol), and the resulting mixture was heated at 80° C. for 15 min. Excess thionylchloride was removed in vacuo to give the title compound as a crude product 2.19 g (80%), used in example 25 without further purification.

Example 24

1-(9H-Carbazol-9-yl)-3-chlorobutan-1-one (Compound 23)

A mixture of compound 22 (1.12 g, 0.0079 mol) and carbazole (1.21 g, 0.0079 mol) in anhydrous toluene (50 mL) was heated at reflux temperature for 72 h. The reaction mixture was concentrated in vacuo, and the residue purified on a silica gel column (Eluent: n-heptane/ethyl acetate (8:1). The isolated product was crystallised from n-heptane/ethyl acetate (8:1) to give the title compound 0.33 g (17%). M.p. 103

Example 25

3-Chloro-1-(9H-Carbazol-9-yl)butane (Compound 24)

To a cooled (5° C.) solution of compound 23 (0.29 g, 0.0011 mol) in anhydrous THF (10 mL) was added boron tetrafluoride diethyl etherate (50% in diethyl ether, 0.20 g) and $NaBH_4$ (0.04 g, 0.0011 mol). The resulting mixture was heated at 50° C. overnight. After aqueous work up of the reaction mixture, the residue was purified on a silica gel column (Eluent: n-heptane/$CH_2Cl_2$ (1:1) to give the title compound 0.10 g (36%) as a colourless oil.

Example 26

1-(3-(9H-Carbazol-9-yl)-1-methyl-1-propyl)-4-phenylpiperidin-4-ol hydrochloride (Compound 25)

A mixture of compound 24 (0.12 g, 0.0048 mol), 4-phenylpiperidin-4-ol (0.10 g, 0.0058 mol), NaI (0.09 g, 0.0006 mol), $K_2CO_3$ (0.20 g, 0.0014 mol) and dry DMF was heated at reflux temperature for 24 h. The reaction mixture was filtered and the solvent removed in vacuo. The residue was purified on a silica

Example 27

1-(3-(9H-Carbazol-9-yl)-2-hydroxy-1-propyl)-4-phenylpiperidin-4-ol hydrochloride (Compound 26)

4-Phenylpiperidin-4-ol (0.77 g, 0.0043 mol) was dissolved in 4-methyl-pentan-2-one (40 mL), $K_2CO_3$ (1.59 g, 0.0116 mol) and 9-(3-chloro-2-hydroxy-1-propyl)carbazole (0.75 g, 0.0029 mol) were added, and the resulting mixture was stirred at reflux temperature overnight. The reaction mixture was filtered and the solvent was removed in vacuo. The residual oil was purified on a silica gel column (Eluent: $CH_2Cl_2$/ethanol/25% $NH_4OH$ (aq) (92.75:7:0.25)), and further purified on a silica gel column (Eluent: Gradient 1) ethyl acetate/methanol (20:1); 2) ethyl acetate/methanol (3:1); 3) $CH_2Cl_2$/methanol (9:1)). The product was acidified with 2M HCl(g) in diethyl ether, to give the title compound 0.77 g (61%). M.p. decomposes at 193–224° C.

Example 28

(S)-1-(3-(9H-Carbazol-9-yl)-2-methyl-1-propyl)-4-(4-methoxyphenyl)piperidin-4-ol hydrochloride (Compound 27)

Compound 10 (2.60 g, 0.0109 mol) was dissolved in anhydrous toluene (50 mL), and the mixture cooled to 2° C. TEA (3.29 g, 0.0326 mol) and methanesulfonylchloride (1.86 g, 0.0163 mol) were carefully added. The resulting mixture was stirred at room temperature for 1.5 h, and water (50 mL) was added. The phases were separated and the organic phase was extracted with water (50 mL). The combined aqueous phases were extracted with toluene (40 mL). The organic phase was washed with brine and dried ($MgSO_4$). The solvent was removed in vacuo to give the crude mesylate (3.2 g). The mesylate (1.55 g, 0.0049 mol) was dissolved in 4-methylpentan-2-one (50 mL). (40 mL). The organic phase was washed with brirne and dried ($MgSO_4$). The solvent was removed in vacuo to give the crude mesylate (3.2 g). The mesylate (1.55 g, 0.0049 mol) was dissolved in 4-methylpentan-2-one (50 mL). 4-(4-Methoxyphenyl)-piperidin-4-ol (1.52 g, 0.0073 mol) and $K_2CO_3$ (2.69 g, 0.0195 mol) were added, and the resulting mixture was heated at reflux temperature for 72 h. The reaction mixture was filtered and the solvent was removed in vacuo. The residual oil was purified on a silica gel column (Eluent: $CH_2Cl_2$/ethanol/25% NH40H (aq) (250:9:1)). The product was acidified with 2M HCl(g) in diethyl ether, to give the title compound 1.23 g (54%). M.p. decomposes at 157° C.

What is claimed is:

1. A compound of formula I

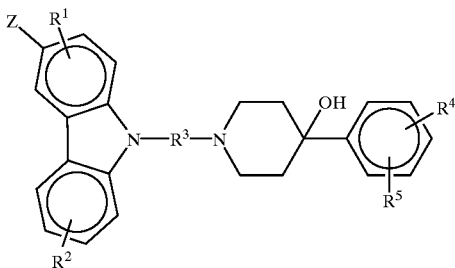
(I)

wherein

R[1] and R[2] independently are hydrogen, halogen, hydroxy, nitro, $-(CH_2)_n-(C=O)-(CH_2)_mCH_3$, $-NR^9R^{10}$, $-SONR^{11}R^{12}$, $-COOR^{13}$, $-CONR^{14}R^{15}$, $C_{1-6}$-alkyl, $C_{1-6}$-alkoxy, trifluoromethyl or trifluoromethoxy wherein $R^9$, $R^{10}$, $R^{11}$, $R^{12}$, $R^{13}$, $R^{14}$ and $R^{15}$ independently are hydrogen, $C_{1-6}$-alkyl, $C_{2-6}$-alkenyl or $C_{2-6}$-alkynyl, and wherein n and m independently are 0, 1, 2, 3 or 4; and $R^3$ is $C_{1-5}$-alkylene optionally substituted with one or two $C_{1-6}$-alkyl; and $R^4$ is hydrogen or $C_{1-6}$-alkyl; and $R^5$ and $R^6$ independently are hydrogen, halogen, hydroxy, nitro, $-NR^{16}R^{17}$, $-COOR^{18}$, $C_{1-6}$-alkyl, $C_{1-6}$-alkoxy, trifluoromethyl or trifluoromethoxy wherein $R^{16}$, $R^{17}$ and $R^{18}$ independently are hydrogen, $C_{1-6}$-alkyl, $C_{2-6}$-alkenyl or $C_{2-6}$-alkynyl; and Z is $-(CH_2)_p-(C=O)-(CH_2)_qCH_3$, $-COOR^{19}$,

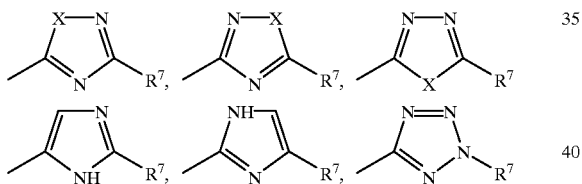

wherein p and q independently are 0, 1, 2, 3 or 4; and $R^{19}$ is hydrogen, $C_{1-6}$-alkyl, $C_{2-6}$-alkenyl or $C_{2-6}$-alkynyl; and X is $-NH-$, oxygen or sulphur; and $R^7$ is hydrogen, $C_{1-6}$-alkyl, $C_{2-6}$-alkenyl, $C_{2-6}$-alkynyl, phenyl, $C_{3-7}$-cycloalkyl, $-OR^8$ or $-SR^8$ wherein $R^8$ is hydrogen or $C_{1-6}$-alkyl; or a pharmaceutically acceptable salt thereof.

2. A compound according to claim 1 which is 1-(3-(9H-Carbazol-9-yl)-1-propyl)-4-(4-methoxyphenyl) piperidin-4-ol, 1-(3-(9H-Carbazol-9-yl)-1-propyl)-4-phenylpiperidin-4-ol, 1-(3-(9H-Carbazol-9-yl)-1-propyl)-4-(2-methoxyphenyl) piperidin-4-ol, 1-(3-(9H-Carbazol-9-yl)-1-propyl)-3-methyl-4-(4-methoxyphenyl) piperidin-4-ol, 1-(3-(9H-Carbazol-9-yl)-1-propyl)-4-(4-chlorophenyl) piperidin-4-ol, (S)-1-((3-(9H-Carbazol-9-yl)-2-methyl)-1-propyl)-4-phenylpiperidin-4-ol, (R)-1-((3-(9H-Carbazol-9-yl)-2-methyl)-1-propyl)-4-phenylpiperidin-4-ol, 1-(3-(9H-Carbazol-9-yl)-1-propyl)-4-(2-tolyl)piperidin-4-ol, 1-(3-(3-Ethyl-9H-carbazol-9-yl)-1-propyl)-4-phenylpiperidin-4-ol, 1-(3-(9H-Carbazol-9-yl)-1-propyl)-4-(2,4-dimethoxyphenyl)piperidin-4-ol, 1-(3-(3-Nitro-9H-carbazol-9-yl)-1-propyl)-4-phenylpiperidin-4-ol, 1-(3-(3-Acetyl-9H-carbazol-9-yl)-1-propyl)-4-phenylpiperidin-4-ol, or a pharmaceutically acceptable salt thereof.

3. A method of preparing a compound according to claim 1, CHARACTERIZED IN a) reacting a compound of formula II

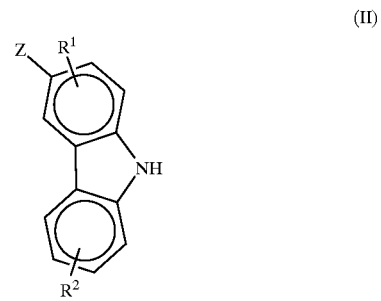
(II)

wherein $R^1$, $R^2$ and Z are as defined above with a compound of formula III

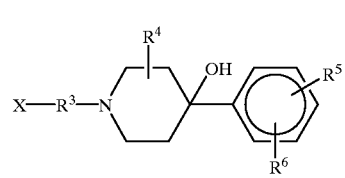
(III)

wherein $R^3$, $R^4$, $R^5$ and $R^6$ are as defined above and X is a leaving group; or b) reacting a compound of formula IV

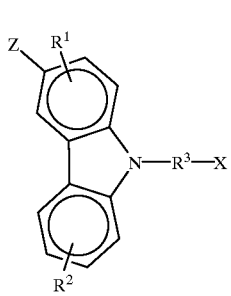
(IV)

wherein $R^1$, $R^2$, $R^3$, Z and X are as defined above with a compound of formula V

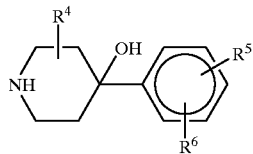
(V)

wherein $R^4$, $R^5$ and $R^6$ are as defined above; or c) reacting a compound of formula VI

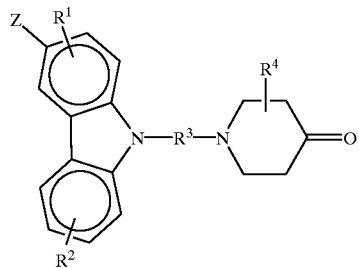
(VI)

wherein $R^1$, $R^2$, $R^3$, $R^4$ and Z are as defined above with a compound of formula VII

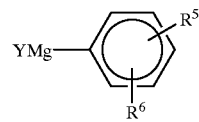
(VII)

wherein $R^5$, $R^6$ and Y are as defined above.

4. A pharmaceutical composition comprising a therapeutically effective amount of a compound according to claim 1 together with a pharmaceutically acceptable carrier or diluent.

5. A pharmaceutical composition suitable for treating a central nervous system ailment related to the inhibition of GABA uptake via the GAT-4 subtype carrier comprising an effective amount of a compound according to claim 1 together with a pharmaceutically acceptable carrier or diluent.

6. The pharmaceutical composition according to claim 4 or 5 comprising between 0.5 mg and 1000 mg of the compound according to claim 1 per unit dose.

7. A method of treating a central nervous system ailment related to the inhibition of GABA uptake via the GAT-4 subtype carrier in a subject in need of such treatment comprising administering to said subject an effective amount of a compound according to claim 1.

8. A method of treating a central nervous system ailment related to the inhibition of GABA uptake via the GAT-4 subtype carrier in a subject in need of such treatment comprising administering to said subject a pharmaceutical composition according to claim 5.

* * * * *